United States Patent
Tokiwa et al.

(10) Patent No.: US 7,439,076 B1
(45) Date of Patent: Oct. 21, 2008

(54) LIQUID DISPENSING METHOD AND DEVICE

(75) Inventors: Yukie Tokiwa, Hitachinaka (JP); Kyoko Imai, Hitachinaka (JP); Lotterer Siegfried, Munich (DE); Krause Friedemann, Penzberg (DE)

(73) Assignees: Hitachi, Ltd., Tokyo (JP); Roche Diagnostics Operations, Inc., Indianapolis, IN (US)

( * ) Notice: Subject to any disclaimer, the term of this patent is extended or adjusted under 35 U.S.C. 154(b) by 432 days.

(21) Appl. No.: 10/311,805

(22) PCT Filed: Jun. 30, 2000

(86) PCT No.: PCT/JP00/04390

§ 371 (c)(1),
(2), (4) Date: Jul. 29, 2003

(87) PCT Pub. No.: WO02/03078

PCT Pub. Date: Jan. 10, 2002

(51) Int. Cl.
*G01N 1/10* (2006.01)
*B01L 3/02* (2006.01)

(52) U.S. Cl. .................. 436/180; 436/174; 422/100; 73/863.32; 73/864

(58) Field of Classification Search .................. 422/100; 436/180, 174; 73/863.32, 864, 864.01, 864.11, 73/864.16
See application file for complete search history.

(56) References Cited

U.S. PATENT DOCUMENTS

| | | | | |
|---|---|---|---|---|
| 4,000,974 A | * | 1/1977 | Acord | 436/54 |
| 4,082,121 A | * | 4/1978 | Sturm et al. | 141/27 |
| 4,821,586 A | * | 4/1989 | Scordato et al. | 73/864.18 |
| 4,905,526 A | * | 3/1990 | Magnussen et al. | 73/864.18 |
| 5,187,990 A | * | 2/1993 | Magnussen et al. | 73/864.18 |
| 5,271,899 A | * | 12/1993 | Carbonari | 422/67 |
| 5,277,871 A | * | 1/1994 | Fujii et al. | 422/70 |
| 5,312,757 A | | 5/1994 | Matsuyama et al. | |
| 5,364,595 A | * | 11/1994 | Smith | 422/100 |
| 5,452,619 A | * | 9/1995 | Kawanabe et al. | 73/864.01 |
| 5,482,861 A | * | 1/1996 | Clark et al. | 436/48 |
| 5,670,114 A | * | 9/1997 | Sakazume et al. | 422/67 |
| 5,744,099 A | * | 4/1998 | Chase et al. | 422/82 |
| 5,820,824 A | * | 10/1998 | Tanaka | 422/100 |
| 5,871,699 A | * | 2/1999 | Ruggeri | 422/100 |
| 5,906,947 A | * | 5/1999 | Bienhaus et al. | 436/518 |

(Continued)

FOREIGN PATENT DOCUMENTS

DE    42 14 430    11/1992

(Continued)

*Primary Examiner*—Brian R. Gordon
(74) *Attorney, Agent, or Firm*—Mattingly, Stanger, Malur & Brundidge, PC (57) ABSTRACT

A method of pipetting an accurate quantity of liquid comprising the steps of drawing water into a pipetting chip (2) from a liquid container (8), drawing air into said tip first slowly at a first rate and then quickly at a second rate to turn said drawn water into a mist of drops in said tip (2) and increase the relative humidity of the air in said tip (2), waiting a preset time period, and drawing a tested liquid into said tip (2).

This makes the quantity of vapor of the tested liquid in said tip (2) very small and constant and thus the accurate quantity of tested liquid can be pipetted.

8 Claims, 5 Drawing Sheets

U.S. PATENT DOCUMENTS

| | | | |
|---|---|---|---|
| 5,948,358 A * | 9/1999 | Saito | 422/64 |
| 6,066,298 A * | 5/2000 | Fukunaga | 422/100 |
| 6,158,269 A * | 12/2000 | Dorenkott et al. | 73/37 |
| 6,218,193 B1 * | 4/2001 | Kraft et al. | 436/180 |
| 6,391,650 B1 * | 5/2002 | Anderson et al. | 436/174 |
| 6,420,186 B1 * | 7/2002 | Berger et al. | 436/180 |
| 6,509,193 B1 * | 1/2003 | Tajima | 436/49 |
| 6,511,850 B1 * | 1/2003 | Vigh et al. | 436/127 |
| 6,576,477 B1 * | 6/2003 | Tokiwa et al. | 436/180 |
| RE38,281 E * | 10/2003 | Tisone | 422/100 |
| 6,645,433 B2 * | 11/2003 | Homberg et al. | 422/100 |
| 6,709,872 B1 * | 3/2004 | Downs et al. | 436/180 |
| 6,773,927 B2 * | 8/2004 | Osawa et al. | 436/180 |
| 6,805,175 B1 * | 10/2004 | Pinkas et al. | 141/130 |
| 7,097,623 B2 * | 8/2006 | Colin et al. | 600/579 |
| 7,097,808 B1 * | 8/2006 | Onuma | 422/63 |
| 7,134,459 B2 * | 11/2006 | Carlson et al. | 141/130 |
| 2001/0016358 A1 * | 8/2001 | Osawa et al. | 436/180 |
| 2001/0055545 A1 * | 12/2001 | Takii et al. | 422/100 |
| 2003/0013200 A1 * | 1/2003 | Pai et al. | 436/54 |
| 2004/0048393 A1 * | 3/2004 | Colin et al. | 436/180 |
| 2004/0265185 A1 * | 12/2004 | Kitagawa | 422/100 |

FOREIGN PATENT DOCUMENTS

| | | |
|---|---|---|
| JP | 63-169565 | 7/1988 |
| JP | 4-274765 | 9/1992 |
| JP | 4-329365 | 11/1992 |
| JP | 9-288112 | 11/1997 |
| JP | 10-123026 | 5/1998 |

* cited by examiner

LIQUID DISPENSING METHOD AND DEVICE

TECHNICAL FIELD

The present invention relates to a liquid handling method and a liquid handling apparatus, particularly to a liquid handling method and a liquid handling apparatus suitable for an automatic analyzing apparatus.

BACKGROUND ART

An automatic analyzing apparatus which pipettes a reagent and a sample into a reaction container and measures the reactant liquid is equipped with a liquid handler which pipettes reagents and samples into reaction containers.

This liquid handler employs a method of using a pipetting probe made of stainless steel to directly pipette a sample or a reagent, washing the probe which touched a sample or a reagent after pipetting, and using the probe again for next pipetting or a method of applying a disposable tip to a pipetting probe before pipetting and replacing the tip by a new one after pipetting. The method of using a disposable tip can avoid liquid carry-overs between samples, between reagents, and between sample and reagent. As carry-overs between samples cause problems in measurement of immune items which have a wide range of measurement of concentration, the method of using a disposable tip has been frequently used for handling of samples.

However, in pipetting by a tip, the quantity of liquid to be pipetted by the tip may vary as the ambient temperature and relative humidity vary. This is because the saturated vapor pressure of the liquid to be pipetted varies by the ambient temperature and relative humidity and, as the result, the vapor pressure of the gas phase in the tip varies and the quantity of liquid drawn by suction will vary even when the syringe operation is kept constant.

Usually, the tip has a greater contact surface between the liquid to be pipetted and the air in the tip or probe than the stainless steel probe. Therefore, the steam pressure of the air in the tip is greatly dependent upon the vapor of liquid to be drawn by suction and is apt to be affected by the ambient temperature and relative humidity.

As an example of trying to solve the above problem, a method of detecting the level of liquid drawn into the nozzle by suction by a sensor is disclosed by Japanese Patent Application Laid-Open No. 9-288112 (1997).

Judging from the above, it is assumed that the aforesaid problem can be solved by keeping the steam pressure of the air in the tip which draws liquid by suction constant. One of possible methods to solve the problem is to fill the tip with liquid such as water which never reacts with the liquid to be pipetted. Substantially, this method draws a preset amount of water into a tip by suction and drawing a sample liquid into the tip by ejecting the water from the tip.

However, experimentally, we have found that this method cannot draw a sample liquid accurately and repeatedly.

DISCLOSURE OF INVENTION

An object of the present invention is to provide a liquid handling method and apparatus suitable to keep the quantity of a sample liquid to the pipetted from being affected by the ambient temperature and relative humidity.

A liquid handling method in accordance with the present invention comprises the steps of drawing a non-reactive liquid into a pipetting probe by suction, drawing air into the probe first slowly at a first rate and then quickly at a second rate, drawing a sample liquid into the probe by suction, and ejecting the drawn sample liquid from the probe.

As already explained, the method comprising the steps of drawing a preset amount of water into a tip by suction and drawing a sample liquid into the tip by ejecting the water from the tip cannot draw a sample liquid accurately and repeatedly. It is assumed that this is because the relative humidity of the air in the tip is low and unstable.

The method in accordance with the present invention draws water into a pipetting probe by suction, draws air into the probe first slowly and then quickly. This turns the drawn water into water mist of drops in the tip (accelerating the vaporization of water), efficiently increases the relative humidity of the air in the tip, and makes the relative humidity in the tip stable. Experimentally, we inventors have found that this method can consequently decrease the influence by the ambient temperature and relative humidity upon the quantity of liquid to be pipetted. Therefore, the present invention is original and novel based upon new facts obtained by the inventors.

Other and further objects, features and advantages of the present invention will appear more fully from the following description.

BEST MODE FOR CARRYING OUT THE INVENTION

Figure 1:
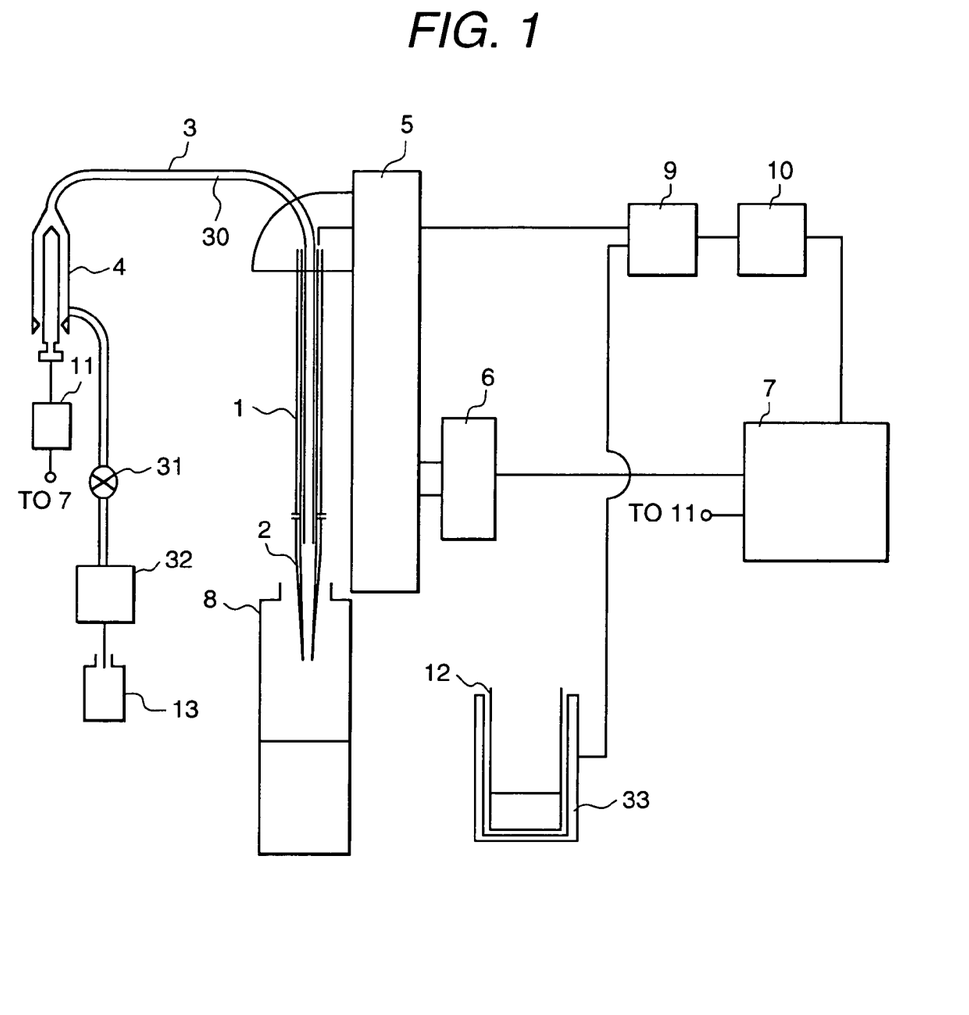
FIG. 1 is a schematic diagram of a liquid handling apparatus according to one embodiment of the present invention.

FIG. 1 is a schematic diagram of a liquid handling apparatus according to one embodiment of the present invention. A conductive pipetting probe 1 has a conductive tip 2 on the lower end of the probe 1. The probe 1 is connected to a syringe 4 with a tube 3. The syringe 4 is driven by a syringe driving mechanism 11 which is controlled by a control section 7. A pump 32 pumps up water from a water tank 13 to fill the syringe 4, the tube 3, and the probe 1 with water prior to pipetting of a sample liquid. A valve 31 is opened to fill them with water. Water is used as medium to transmit operation of the syringe 4 to a sample liquid when drawing a sample liquid into a tip 2 by suction and ejecting the sample liquid from the tip 2. The transmitting medium is assigned a symbol 30 in the accompanying drawings.

A probe lifting and transferring mechanism 5 driven by a motor 6 can move the probe up and down and the motor 6 is controlled by a control section 7. The probe 1 horizontally moved among a tip mounting position, sample/reagent drawing/ejecting positions, and a tip demounting position. This horizontal movement of the probe 1 is controlled by the control section 7.

A container holder 33 made of a conductive material holds a liquid container 12 which is made of a non-conductive material such as glass of plastic resin. The liquid container 12 contains a sample or reagent. The probe 1 and the container holder 33 are connected to a static capacity measuring section 9 to which a level judging section 10 is connected. The level judging section 10 is further connected to the control section 7.

When the pipetting probe 1 goes down by the probe lifting and transferring mechanism 5 and the conductive tip 2 touches a liquid in the liquid container 12, the static capacity between the conductive probe 1 and the container holder 33 varies. The static capacity measuring section 9 measures the static capacity. The level judging section 10 detects a change in the static capacity and sends it as a liquid level signal to the control section 7.

When the probe 1 stops going down, the syringe 4 works to draw a sample liquid into the tip 2. The syringe 4 also works to discharge the sample liquid from the tip 2.

A liquid container 8 is provided to contain a non-reactive liquid such as water which does not react with a liquid to be pipetted. The non-reactive liquid such as water is drawn from the liquid container 8 into the tip 2 to increase the relative humidity of the air in the tip 2 before the liquid to be pipetted is drawn into the tip 2 by suction.

Figure 2:
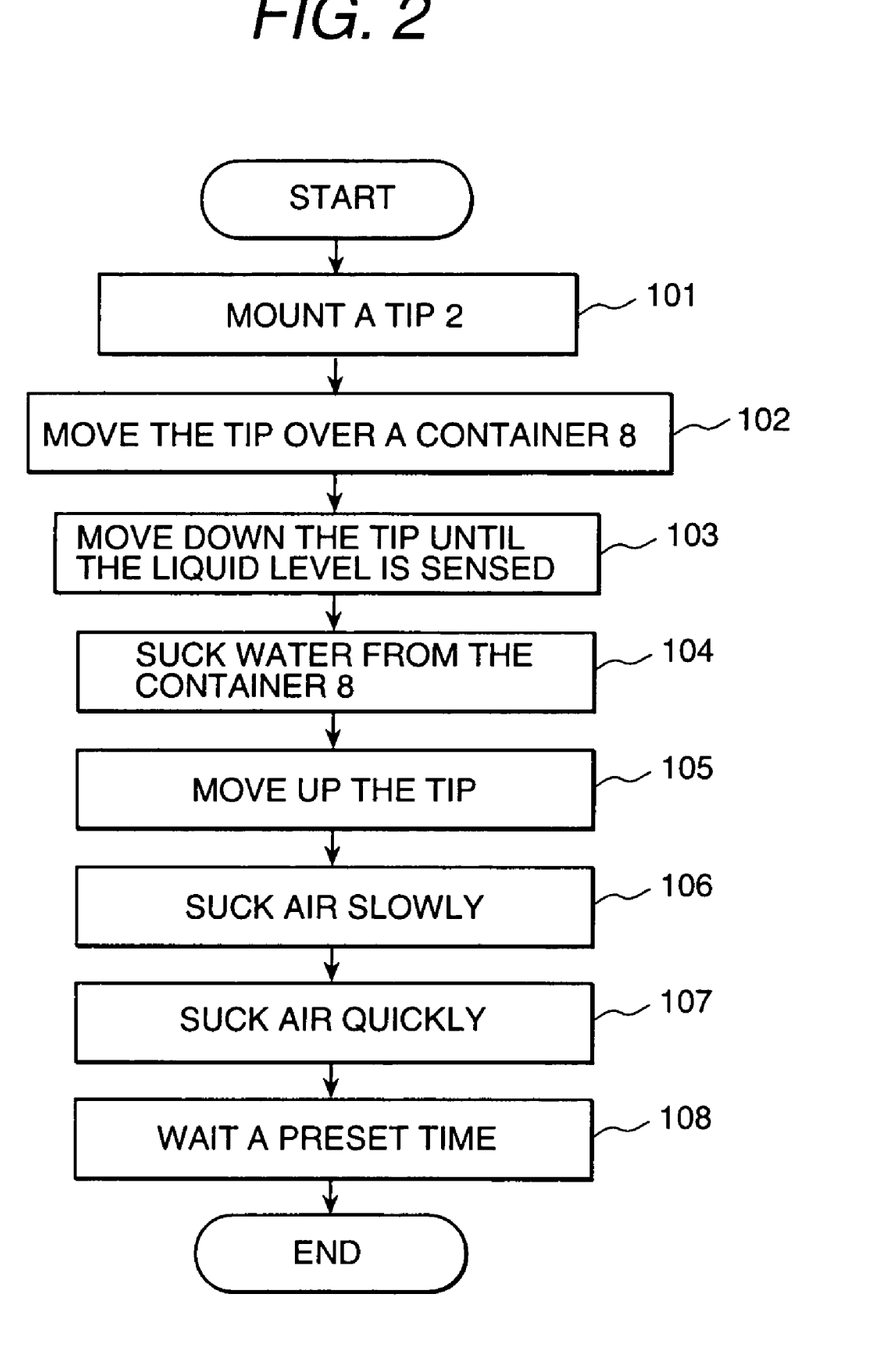
FIG. 2 is an operation flow of the pipetting probe before a sample liquid is drawn into the tip by suction.

FIG. 2 shows an operation flow of the pipetting probe 1 before a sample liquid is drawn into the tip 2 by suction. Step 101 mounts a tip 2 on the pipetting probe 1 at the tip mounting position (to be explained later). Step 102 moves the probe 1 with the tip 2 over the liquid container 8 on the automatic analyzing unit. The liquid container 8 can be installed under the tip mounting position. Then, the probe lifting and transferring mechanism 5 moves the probe down into the liquid container 8 until the lower end of the tip 2 touches the liquid in the liquid container 8 and stops moving down the probe when the tip 2 touches the liquid surface (Step 103).

Step 104 draws a preset amount of the non-reactive liquid (water) from the liquid container 8 into the tip 2 on the lower end of the probe 1 by the syringe 4. The preset amount of water to be drawn is about 4 µl.

After drawing water into the tip, the probe 1 moves up (Step 105) and draws air slowly into the tip by suction (Step 106). For example, an air of 30 µl is taken in at a rate of 30 µl/s. The water drawn into the tip 2 is a layer of thickness less than 1 mm in the tip 2.

Next, the probe 1 draws air quickly into the tip by suction (Step 107). For example, an air of 50 µl is taken in at a rate of 150 µl/s. The layer of water in the tip bubbles up and water turns into water mist or drops. This step can accelerate vaporization of water, efficiently increase the relative humidity of air in the tip and keep it steady.

For a preset time period (e.g. 2 seconds later), the probe 1 moves to the liquid suction position and draws a liquid to be pipetted into the liquid container 12 by suction (Step 104).

With this, the quantity of vapor of the liquid in the tip 2 is small enough to be ignored and an exact amount of liquid can be pipetted substantially without being influenced by the ambient temperature and relative humidity.

Figure 3:
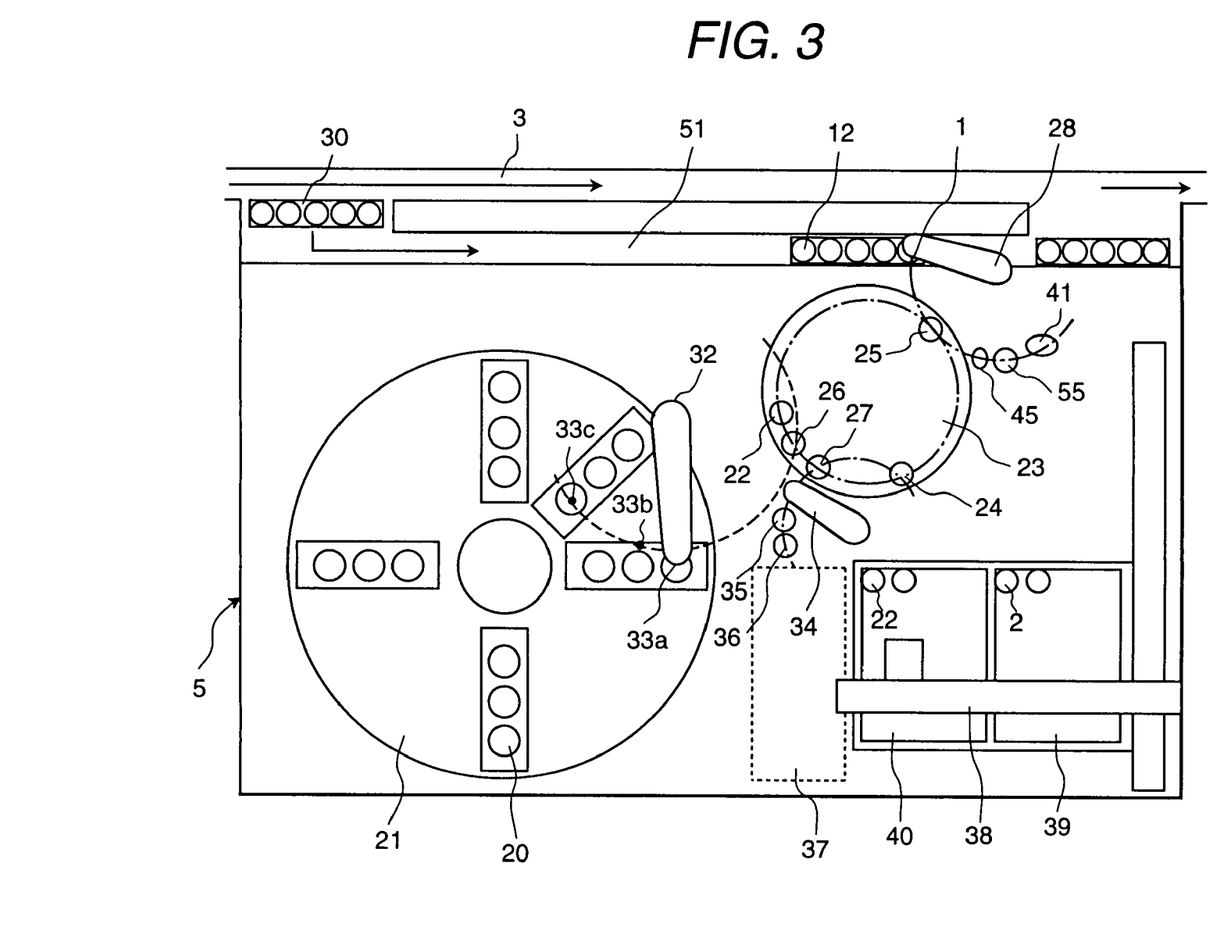
FIG. 3 is a plan view of an automatic analyzing unit using the liquid handling apparatus according to one embodiment of the present invention.

FIG. 3 is a plan view of an automatic analyzing unit using the liquid handling apparatus according to one embodiment of the present invention. This embodiment is suitable for analysis of immune items. A plurality of liquid containers 20 are arranged in three concentric circles on a reagent disk 21 which is rotated by a motor. A plurality of reaction containers 22 are disposed in a circle on a thermostatic bath 23 which is rotated by a motor. As the thermostatic bath 23 rotates, the reaction containers 22 are transferred from the reaction container setting position 24 to the reagent pipetting position 26, the sample pipetting position 25, and the reactant suction position 27.

The reagent probe 32 can be rotated by a motor between the reagent suction position and the reagent pipetting position 26. The reagent pipetting position comprises a pipetting position 33a for a liquid container 20 on the outermost circle, a pipetting position 33b for a liquid container 20 on the center circle, and a pipetting position 33c for a liquid container 20 on the innermost circle.

The sample pipetting probe 1 can be rotated by a motor among the sample suction position 29, the sample pipetting position 25, the non-reactive liquid suction position 45, the tip mounting position 55, and the tip demounting position 41. A liquid container 8 of FIG. 1 is disposed at the non-reactive liquid suction position 45 and filled with a non-reactive liquid such as water. The non-reactive liquid suction position 45 can be at the tip mounting position 55. In this case, the liquid container 8 for non-reactive liquid is placed below the tip mounting position 55.

The sample rack 30 is transferred from the conveying line to the lead-in line 51. When a sample is transferred from a liquid container 12 in the sample rack at the sample suction position 29 to a reaction container 22 at the sample pipetting position 25, a disposable tip 2 is mounted on the lower end of the sample probe 1. Of course, the disposable tip 2 is removable.

The sipper 34 can be rotated by a motor among the reactant suction position 27, the buffer solution suction position 35, and a flow cell washing position 36. The sipper 34 has a function of sending a reactant liquid to a flow cell in the detection unit 37 by means of a tube.

The mechanism 38 for transferring tips and the reaction containers transfers a disposable tip 2 from the tip rack 39 to the tip mounting position 55 and a reaction container 22 from the reaction container rack 40 to the reaction container setting position 24. The reagent probe 32 and the sipper 34 respectively wash their nozzles at the washing positions (not visible in FIG. 3).

The sample probe 1, the reagent probe 32, and the sipper can move up and down respectively at their stop positions.

Figure 4:
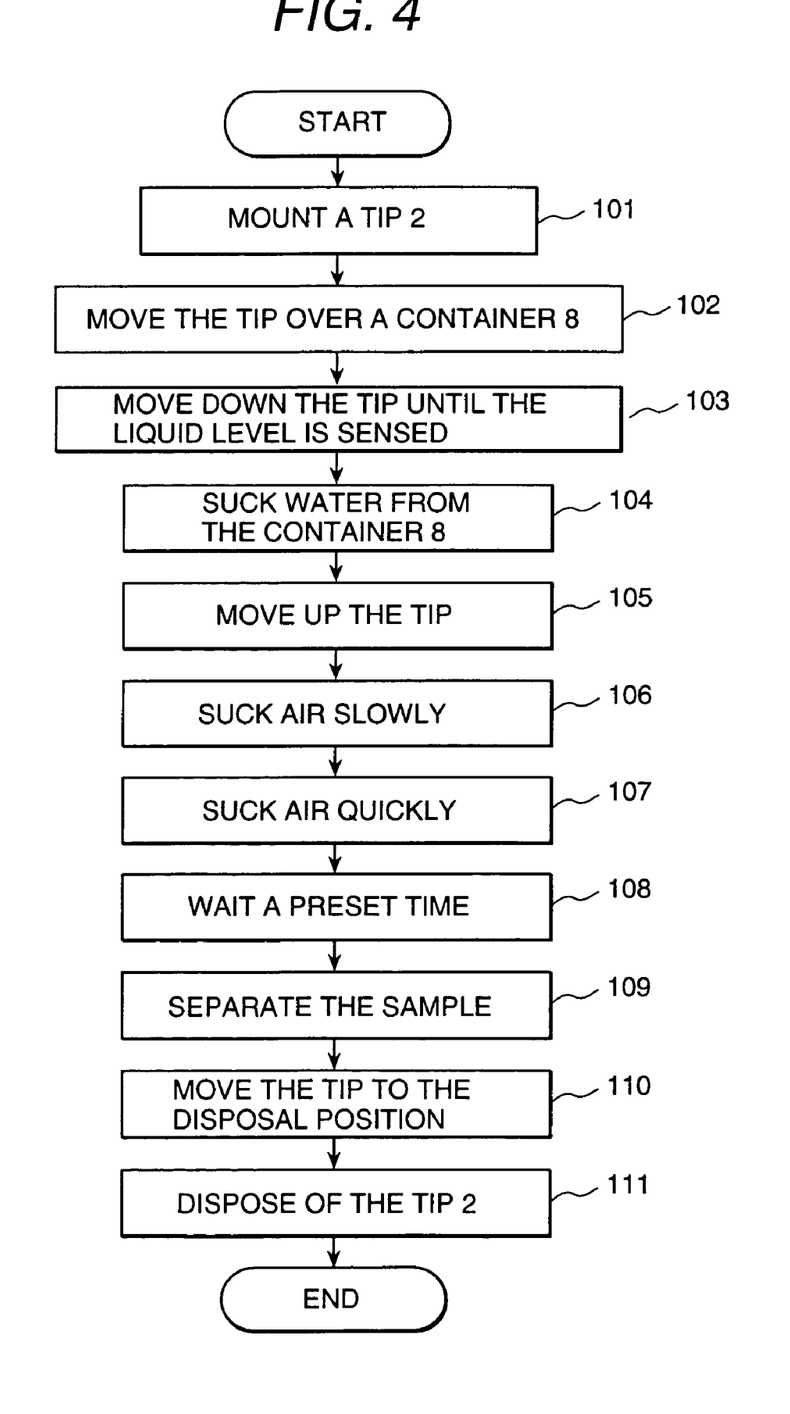
FIG. 4 is a whole pipetting flow of the embodiment of FIG. 3.

Referring to FIG. 3 and FIG. 4, the mechanism 38 for transferring tips and the reaction containers transfers a disposable tip 2 from the tip rack 39 to the tip mounting position 55 and a reaction container 22 from the reaction container rack 40 to the reaction container setting position 24. The sample probe 1 moves to the tip mounting position 55 and mounts a disposable tip 2 on the lower end of the probe 1 at the tip mounting position 55 (Step 101). The probe 1 with the tip 2 moves to the non-reactive liquid suction position 45 (Step 102), moves down into the liquid container 8 until the tip 2 touches the surface of the non-reactive liquid (water) (103), draws water (Step 104), moves up (Step 105), and draws air into the tip 2 by suction first slowly and then quickly (Step 106 and Step 107). The water suction speed, the quantity of sucked water, air suction speeds, and the quantities of sucked water are the same as those in the description of FIG. 1 and FIG. 2.

A reaction container 22 is transferred from the reaction container setting position 24 to the reagent suction position 26.

The reagent probe 32 moves to the reagent pipetting position 33a, 33b, or 33c, moves down there, draws the reagent there by suction, moves up, moves to the reagent pipetting position 26, discharges the reagent into the reaction container 22, and moves up.

The reaction container 22 is moved to the sample pipetting position 25.

After a preset time period (Step 108), the sample probe 1 pipettes the sample liquid (Step 109), moves to the tip disposal position (Step 110), and disposes of the tip 2.

Figure 5:
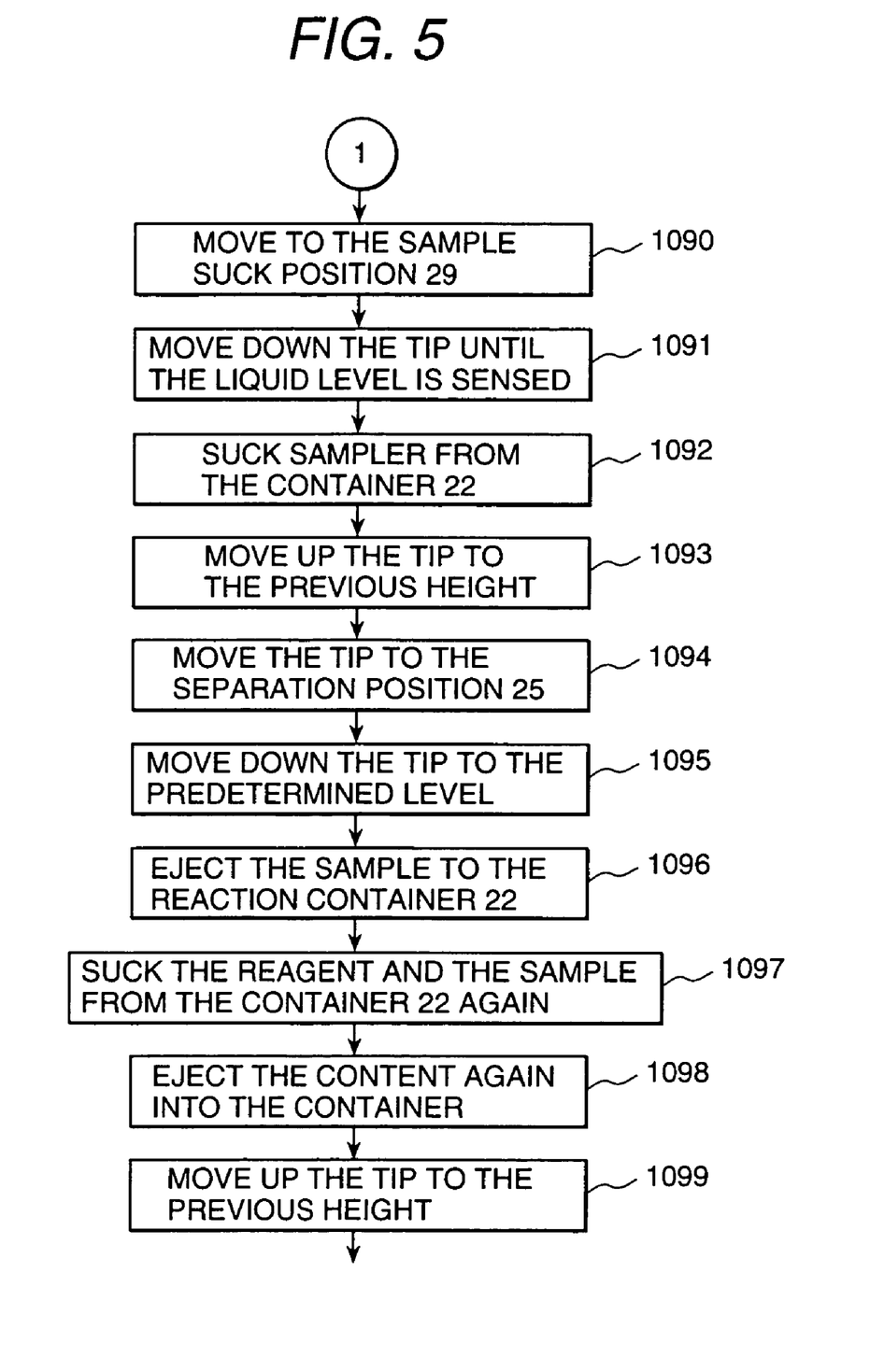
FIG. 5 is a sample liquid pipetting flow.

Step 109 and later steps will be explained in more detail referring to FIG. 3 to FIG. 5.

The sample probe 1 moves to the sample suction position 29 (Step 1090), moves down into the liquid container 12 at the suction position 29 until the surface of the sample liquid to be pipetted is detected (Step 1091), draws the sample into the tip 2 on the lower end of the sample probe 1 by suction (1092), move back to the original height (Step 1093), moves to the sample pipetting position 25 (Step 1094), moves down by a preset distance (Step 1095), discharges the sample liquid into the reaction container 22 containing the reagent at the sample pipetting position (Step 1096), moves down again into the reaction container at the sample pipetting position 25, draws a mixture of the sample and the reagent from the reaction container 22 at the sample pipetting position into the tip 2 on the lower end of the sample probe 1 by suction (1097), discharges the drawn mixture again into the reaction container 22 from the tip 2 (Step 1098), and moves back to the original height. Step 1098 is to stir the mixture completely and accelerate its reaction. The sample probe 1 moves to the tip disposal position 41 (Step 110) and disposes of the tip there (Step 111).

A preset time period in step 108 means a time period between a suction of air into the tip 2 of the sample pipetting probe 1 and a suction of a sample and is equal to the time in the description of FIG. 1 and FIG. 2.

The reaction container 22 containing a reactant liquid is moved to the reactant liquid suction position 27. The sipper 34 draws up the reactant liquid by suction from the reaction container 22, moves to the buffer solution liquid suction position 35, draws up the buffer solution by suction, and transfers it into the flow cell in the detection unit 37 through a tube. The detection unit measures the chemiluminescence of the reactant liquid in the flow cell. Thus, the result of analysis of immune items is obtained.

Then, the sipper 34 moves to the flow cell washing position 36, draws up the flow cell washing liquid, feeds the washing liquid to the flow cell through a tube and washes the flow cell.

The embodiment of FIG. 3 employs the steps of mounting a disposable tip on the lower end of the sample probe and drawing non-reactive liquid into the tip by suction before sample suction. However, it is also preferable to add steps of mounting a disposable tip on the lower end of the reagent probe and drawing non-reactive liquid into the tip by suction before sample suction.

Table 1 shows the result of experiments on accuracy and reproducibility of liquid pipetting at a room temperature of 32° C. and relative humidity of 20% which is severe for pipetting because this condition will accelerate vaporization.

TABLE 1

|  | Comparative Example 1 | Comparative Example 2 | Embodiment of Invention |
|---|---|---|---|
| Accuracy (%) | 87 | 92 | 97 |
| Precision (%) | 4.3 | 1.5 | 0.6 |

The comparative example 1 comprises the steps of sucking water of 50 µl, ejecting thereof, and sucking a sample. The comparative example 2 comprises the steps of sucking water of 4 µl, sucking air of 30 µl, waiting for 2 seconds, and sucking a sample. The embodiment of the invention comprises the steps of sucking water of 4 µl, sucking air of 30 µl at a rate of 30 µl/s, sucking air of 50 µl at a rate of 150 µl/s, waiting for 2 seconds, and sucking a sample. Each example pipetted ten times. The "Accuracy" value means the quotient of the average of actually-pipetted sample liquids by the quantity of sample liquid to be pipetted ×100. The "Precision" value means the quotient of the standard deviation of actually-pipetted sample liquids by the quantity of average of actually-pipetted sample liquids to be pipetted ×100.

It is apparent from Table 1 that embodiment of the invention has improved the pipetting accuracy from 87% (as comparative example 1) and 92% (as comparative example 2) to 97% (as the embodiment of the invention). Similarly, it is apparent from Table 1 that embodiment of the invention has improved the pipetting reproducibility from 4.3% (as comparative example 1) and 1.5% (as comparative example 2) to 0.6% (as the embodiment of the invention).

For analysis using tips, it is not allowed to use an identical stirring rod to stir a mixture of a sample and a reagent in a reaction container to prevent carry-overs between samples and reagents. Therefore, the sample and the reagent in a tip are re-drawn by suction and re-discharged into the reaction container to stir the mixture. In this case, the comparative example 2 may cause immigration of water (which was sucked into the tip) into the mixture of the sample and the reagent.

However, the present invention which generates water mist in the tip or very fine water drops in the upper end of the tip substantially never causes immigration of water into the mixture of the sample and the reagent and the pipetting precision is good.

As seen from the aforesaid description, the embodiments of the present invention can lighten the influence due to the ambient temperature and relative humidity upon the quantities of pipetted liquid.

It is apparent that various changes and deformations may be made within the scope of the present invention. The embodiments are not intended as a definition of the limits of the invention.

The invention claimed is:

1. A liquid handling method comprising the steps of ejecting a drawn liquid to be tested from a pipetting probe with removable tip after first drawing non-reactive liquid into said probe by suction, drawing air into said probe at a first rate and then at a second rate quicker than said first rate, said step of drawing air generates mist in the tip or very fine drops in an upper end of the tip increasing the relative humidity of air in the tip, and drawing said liquid to be tested into the probe by suction.

2. A liquid handling method in accordance with claim 1, wherein a preset time period is provided between said step of drawing air at the second rate and drawing said liquid to be tested into the probe.

3. A liquid handling method in accordance with claim 2, wherein said step of drawing non-reactive liquid into said probe draws water into said probe as said non-reactive liquid and said step of drawing said liquid to be tested into the probe draws a sample into said probe as said liquid to be tested.

4. A liquid handling method in accordance with claim 1, wherein said drawing of air into said probe at said second rate draws air at a rate sufficient to cause a layer of non-reactive liquid in the tip to bubble up and turn into mist or drops.

5. A liquid handling method in accordance with claim 1, wherein said step of first drawing non-reactive liquid into said probe draws water into said probe as said non-reactive liquid and said step of drawing air draws air at a rate sufficient to generate at least one of water mist in the tip and very fine water drops in the upper end of the tip increasing relative humidity of air in the tip.

6. A liquid handling method in an automatic analyzer that pipettes a liquid into a reaction container using a pipetting probe with a removable tip, comprising the steps of:

first drawing water into said pipetting probe by suction;

second drawing air into said probe at a first rate and then drawing air into said probe at a second rate that is greater than said first rate such that said step of drawing air causes a layer of water in the tip to generate at least one of water mist in the tip and very fine drops of water in an upper end of the tip to increase a relative humidity of air in the tip;

third drawing a liquid of a predetermined volume into said pipetting probe by suction; and discharging the liquid into the reaction container from the pipetting probe.

7. A liquid handling method in accordance with claim 6, wherein in said second step of drawing air, said second rate of drawing air is at least twice that of said first rate of drawing air into said probe.

8. A liquid handling method in accordance with claim 6, wherein in said first step of drawing water, said layer of water drawn in is less than 1 mm.

* * * * *